United States Patent
Dubois

(10) Patent No.: US 7,880,034 B2
(45) Date of Patent: Feb. 1, 2011

(54) ACRYLIC ACID PREPARATION METHOD

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 281 days.

(21) Appl. No.: 12/278,016

(22) PCT Filed: Feb. 6, 2007

(86) PCT No.: PCT/FR2007/050758

§ 371 (c)(1),
(2), (4) Date: Aug. 1, 2008

(87) PCT Pub. No.: WO2007/090991

PCT Pub. Date: Aug. 16, 2007

(65) Prior Publication Data

US 2009/0018362 A1     Jan. 15, 2009

(30) Foreign Application Priority Data

Feb. 7, 2006    (FR) .................................. 06 01061

(51) Int. Cl.
*C07C 51/16* (2006.01)
(52) U.S. Cl. .................. 562/545; 562/546; 562/547
(58) Field of Classification Search ................. 562/545, 562/546, 547
See application file for complete search history.

(56) References Cited

U.S. PATENT DOCUMENTS

| | | | |
|---|---|---|---|
| 2,558,520 A | 6/1951 | Hoyt et al. | |
| 5,218,146 A | 6/1993 | Takata et al. | |
| 5,387,720 A | 2/1995 | Neher et al. | |
| 6,080,898 A | 6/2000 | Drent et al. | |
| 2004/0220434 A1 | 11/2004 | Brophy et al. | |
| 2007/0129570 A1 | 6/2007 | Shima et al. | |

FOREIGN PATENT DOCUMENTS

| | | |
|---|---|---|
| EP | 257565 | 9/1988 |
| EP | 0293224 | * 11/1988 |
| EP | 995491 | 4/2000 |
| EP | 1147807 | 10/2001 |
| FR | 695931 | 5/1930 |
| GB | 1152215 | 5/1969 |

OTHER PUBLICATIONS

Bicker et al, Catalytic dehydration of glycerol in sub- and supercritical water: a new chemical process for acrolein production, 2006, Green Chemistry, vol. 8, p. 214-220.*
Edition Technip; Marcilly, C.; 200;, p. 71.

* cited by examiner

*Primary Examiner*—Taylor Victor Oh
(74) *Attorney, Agent, or Firm*—Steven D. Boyd

(57) ABSTRACT

The invention relates to a method for preparing acrylic acid from propylene, comprising the oxidation of propylene to acrolein and a second step comprising the oxidation of acrolein to acrylic acid, including a glycerol dehydration step preformed in the presence of a gas containing propylene and, more specifically, in the presence of the reaction gas originating from the propylene to acrolein oxidation step. The inventive method enables the use, in part, of renewable raw material, while increasing acrylic acid production.

6 Claims, 3 Drawing Sheets

ACRYLIC ACID PREPARATION METHOD

TECHNICAL FIELD

The present invention relates to a process for the preparation of acrylic acid from propylene comprising a first stage of oxidation of the propylene to give acrolein and a second stage of oxidation of the acrolein to give acrylic acid, in which use is made of a stage of dehydration of glycerol in the presence of a gas comprising propylene and more particularly in the presence of the reaction gas resulting from the stage of oxidation of the propylene to give acrolein.

BACKGROUND OF THE INVENTION

The conventional process for the synthesis of acrylic acid uses a catalytic reaction of propylene using a mixture comprising oxygen. This reaction is generally carried out in the vapor phase and most often in two stages:

the first stage carries out the substantially quantitative oxidation of the propylene to give a mixture rich in acrolein, in which acrylic acid is a minor component, the second stage carries out the selective oxidation of the acrolein to give acrylic acid.

The reaction conditions of these two stages, carried out in two reactors in series, are different and require catalysts suited to the reaction. It is not necessary to isolate the acrolein during this two-stage process. The reaction can also be carried out in a single reactor but, in this case, it is necessary to separate and recycle large amounts of acrolein in the oxidation stage.

In a certain number of cases, it may be advantageous to be able to increase the acrylic acid production capacities of existing units.

The production of acrylic acid is highly dependent on the propylene starting material. Propylene, obtained by steam cracking or catalytic cracking of petroleum fractions, has the disadvantage of contributing to increasing the greenhouse effect due to its fossil origin. Furthermore, propylene resources may become limited.

It thus appears particularly advantageous to be able to increase the productive output of acrylic acid while reducing the dependency on a fossil resource.

It has been known for a long time that glycerol can result in the production of acrolein. Glycerol results from the methanolysis of vegetable oils, at the same time as the methyl esters, which are themselves employed in particular as fuels in diesel oil and heating oil. This is a natural product which enjoys a "green" aura, it is available in large amount and can be stored and transported without difficulty. Numerous studies are devoted to giving an economic value to glycerol according to its degree of purity and the dehydration of glycerol to give acrolein is one of the roots envisaged.

The reaction involved in producing acrolein from glycerol is:

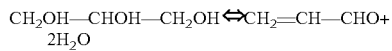

Generally, the hydration reaction is promoted at low temperatures and the dehydration reaction is promoted at high temperatures. In order to obtain acrolein, it is thus necessary to employ a satisfactory temperature and/or a partial vacuum in order to displace the reaction. The reaction can be carried out in the liquid phase or the gas phase. This type of reaction is known to be catalyzed by acids. Various processes for the synthesis of acrolein from glycerol are described in the prior art; mention may in particular be made of the documents FR 695 931, U.S. Pat. No. 2,558,520, WO 99/05085 and U.S. Pat. No. 5,387,720.

The document WO 2005/073160 describes a process for the preparation of acrylic acid from glycerol in two stages, the first stage consisting in subjecting the glycerol to a gas-phase dehydration reaction and the second stage consisting in subjecting the gaseous reaction product thus obtained to a gas-phase oxidation reaction.

It has now been found that the dehydration reaction of glycerol to give acrolein can be carried out in the presence of a gas comprising propylene and more particularly in the presence of the reaction gas resulting from the stage of oxidation of the propylene to give acrolein. It is thus advantageous to introduce glycerol into the conventional process of gas-phase catalytic oxidation of propylene in two stages in order to prepare acrylic acid, which makes it possible to use a renewable starting material while increasing the production of acrylic acid. Such a process then corresponds to the criteria associated with the new concept of "green chemistry" in a more general context of sustainable development.

SUMMARY OF THE INVENTION

The subject matter of the present invention is thus a process for the preparation of acrylic acid from propylene comprising a first stage of oxidation of the propylene to give acrolein and a second stage of oxidation of the acrolein to give acrylic acid, characterized in that it comprises a stage of dehydration of glycerol in the presence of a gas comprising propylene.

Preferably, the gas comprising propylene is the reaction gas resulting from the stage of oxidation of propylene to give acrolein.

Without the Inventor being committed to any one explanation, it believes that the stage of dehydration of the glycerol makes it possible to cool the reaction gases resulting from the first stage of oxidation of the propylene to give acrolein, before carrying out the second stage of oxidation of the acrolein to give acrylic acid.

This is because, in the reaction for the oxidation of propylene to give acrolein, the reaction gases exit from the reaction region at a high temperature, the reaction for the oxidation of propylene being exothermic. In a two-stage process for the preparation of acrylic acid from propylene, it is necessary to cool the reaction gases resulting from the first stage of oxidation of the propylene to give acrolein before entering the second stage of oxidation of the acrolein to give acrylic acid as the reaction for the oxidation of acrolein to give acrylic acid is carried out at a lower temperature than the reaction for the oxidation of propylene to give acrolein. Furthermore, the acrolein can self-ignite at high temperatures, resulting in losses in yields.

This cooling is generally obtained by virtue of a heat exchanger placed downstream of the catalytic region of the first stage. The same effect can, in all or part, be obtained by virtue of the use of an endothermic reaction, such as the dehydration of glycerol. In the present invention, the dehydration reaction of glycerol exhibits the advantage of resulting in the same main reaction product (acrolein) as the reaction for the oxidation of propylene. This thus results in an increase in the productive output of acrolein, while efficiently recovering the heat of the oxidation reaction, and consequently an increase in the productive output of acrylic acid.

BRIEF DESCRIPTION OF THE DRAWINGS

Other characteristics and advantages of the invention will more clearly emerge on reading the description which follows, with reference to the appended figures, in which.

DETAILED DESCRIPTION OF THE INVENTION

Figure 1:
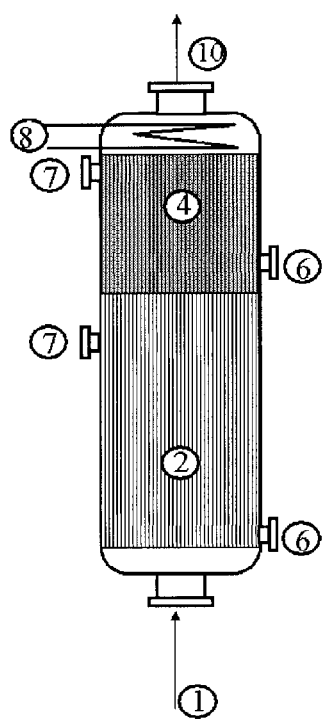
FIGS. 1, 2 and 3 diagrammatically represent conventional configurations for the oxidation of propylene to give acrylic acid in two stages.

In the process of the invention, the stage of dehydration of glycerol is carried out in the gas phase in the presence of a catalyst at a temperature ranging from 150° C. to 500° C., preferably between 250° C. and 350° C., and a pressure of between 1 and 5 bar.

The stage of dehydration of glycerol is carried out upstream of the reaction for the catalytic oxidation of propylene to give acrolein in the presence of the feed gas comprising propylene, or downstream of the reaction for the catalytic oxidation of propylene to give acrolein in the presence of the gas mixture resulting from this reaction. It can be incorporated directly in the oxidation reactor or can be carried out in a reactor placed immediately upstream or downstream of the reactor for the oxidation of propylene to give acrolein. As the dehydration reaction is slightly endothermic, it is not necessary to have a multitubular bed for this reaction. The conventional fixed bed and a configuration as modules (sheets or pans) may be suitable. The modules exhibit the advantage of being able to be easily charged and discharged when the catalyst is deactivated.

The catalysts which are suitable are homogeneous or multiphase materials which are insoluble in the reaction medium and which have a Hammett acidity, recorded as $H_0$, of less than +2. As indicated in U.S. Pat. No. 5,387,720, which refers to the article by K. Tanabe et al. in "Studies in Surface Science and Catalysis", Vol. 51, 1989, chap. 1 and 2, the Hammett acidity is determined by amine titration using indicators or by adsorption of a base in the gas phase. The catalysts corresponding to the criterion of $H_0$ acidity of less than +2 can be chosen from siliceous materials (natural or synthetic) or acid zeolites; inorganic supports, such as oxides, covered with mono-, di-, tri- or polyacidic inorganic acids; oxides or mixed oxides or also heteropolyacids.

Advantageously, the catalysts are chosen from zeolites, Nafion® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$ functional groups. According to the literature data, these catalysts all have a Hammett acidity $H_0$ of less than +2.

The preferred catalysts are sulfated zirconias, phosphated zirconias, tungstated zirconias, silica zirconias, sulfated titanium or tin oxides, or phosphated aluminas or silicas.

These catalysts all have a Hammett acidity $H_0$ of less than +2; the acidity $H_0$ can then vary to a large extent, down to values which are at least −20 in the reference scale with Hammett indicators. The table given on page 71 of the publication on acid/base catalysis (C. Marcilly), Vol. 1, in Editions Technip (ISBN No. 2-7108-0841-2), illustrates examples of solid catalysts within this acidity range.

The glycerol is used pure or in the form of a concentrated or dilute aqueous solution. Advantageously, use is made of pure glycerol or of an aqueous glycerol solution with a concentration ranging from 10% to 100% by weight, preferably ranging from 50% to 100% by weight, when used downstream of the oxidation of the propylene; the steam present in the reaction gas resulting from the stage of oxidation of the propylene to give acrolein makes it possible to dilute the glycerol solution and thus to prevent side reactions, such as the formation of glycerol ethers or reactions between the acrolein produced and the glycerol. In the embodiment of the invention where the stage of dehydration of glycerol is carried out upstream of the reaction for the catalytic oxidation of the propylene, use may be made of an aqueous glycerol solution, preferably with a concentration ranging from 10% to 50% by weight, more particularly from 15% to 30% by weight.

The glycerol can be injected in the liquid form or in the gas form. Injection in the liquid form makes it possible to benefit from the latent heat of vaporization of the glycerol, thus making it possible to cool the gases resulting from the upstream stage of oxidation of the propylene. In this case, the dehydration catalyst can be preceded by a bed of inert materials on which vaporization of the glycerol is carried out. It can be injected in the gas form at a temperature lower than that of the gases exiting from the oxidation region, which makes it possible to further intensify the effect of cooling these gases. Furthermore, the glycerol can be injected under pressure, so that the reduction in pressure of the gas makes possible an additional sorption of heat.

The gas mixture which feeds the reactor for the first stage of oxidation of the propylene to give acrolein is generally composed of propylene, steam, an inert gas, which can be nitrogen or argon, and molecular oxygen or a gas comprising molecular oxygen.

The reaction gas resulting from the stage of oxidation of the propylene to give acrolein is generally composed of a mixture of the unreacted gases (unconverted propylene, propane initially present in the propylene, inert gas, steam, oxygen, CO, $CO_2$), of acrolein produced and of various by-products, such as acrylic acid, acetic acid and other minor compounds.

The reaction for the dehydration of glycerol in the process according to the invention consequently takes place in the presence of molecular oxygen, which occurs either in the gas mixture which feeds the reactor for the first stage of oxidation of the propylene to give acrolein or in the gas mixture resulting from the stage of oxidation of the propylene to give acrolein. The molecular oxygen can be present in the form of air or in the form of a gas mixture comprising molecular oxygen. According to one embodiment of the invention, it is possible to add an additional amount of molecular oxygen or of a gas comprising molecular oxygen for the stage of dehydration of the glycerol. The amount of oxygen is chosen so as to be outside the flammability range and all points of the plant. The presence of oxygen makes it possible to limit the deactivation of the dehydration catalyst by coking. Furthermore, the addition of oxygen improves the reaction yield for numerous catalytic systems.

The reaction for the catalytic oxidation of propylene to give acrylic acid in two stages in the process according to the invention is carried out according to conditions known to a person skilled in the art by passing a gas mixture, which can comprise propylene, steam, an inert gas, which can be nitrogen or argon, and molecular oxygen or a gas comprising molecular oxygen, over a catalyst for the oxidation of the propylene in order to obtain a gas mixture rich in acrolein. Then, the reaction for the selective oxidation of the acrolein to give acrylic acid is carried out over a catalyst suitable for the oxidation of the acrolein. The process can be carried out in just one reactor or in two reactors placed in series. The reactors are generally fixed-bed multitubular reactors. It is also possible to use a plate exchanger with a modular arrangement of the catalyst, such as described in the documents EP 995 491, EP 1 147 807 or US 2005/0020851.

In the case where catalytic oxidation of the propylene is carried out in the presence of a thermal ballast, such as described, for example, in the document EP 293 224 A1, making possible the use of a higher propylene flow rate, the gas mixture resulting from the reaction has a higher specific heat Cp. The process according to the invention is particularly advantageous in this case for discharging the excess heat transported by the reaction gases.

A preferred embodiment of the invention consists in using propane as inert gas as replacement in all or part for the nitrogen of the air. The propane, by virtue of its higher specific heat, carries more heat to the reactor, which makes it possible to more easily carry out the reaction for the dehydration of the glycerol. The gas resulting from the dehydration stage then comprises, as main constituents, steam, propane, acrolein and residual oxygen. This gas then directly feeds the stage of oxidation of the acrolein to give acrylic acid. In this case, the propane is of use in carrying away the heat from the oxidation reaction, which is highly exothermic. After absorption of the acrylic acid, the gases rich in propane can be recycled to the dehydration stage. Preferably, the gas is subjected to purification treatments in order to remove impurities which may be harmful for the dehydration and oxidation reactions, such as CO and/or $CO_2$, and in order to limit the concentration of these impurities in the recycle loop. In this case, it is particularly advantageous to control the concentration of argon in the gas loop on account of its very low specific heat. Mention may be made, as separation techniques which can be used alone or in combination, of the selective oxidation of CO to give $CO_2$, washing with amines, washing with potassium hydroxide, adsorption techniques, membrane separation or cryogenic separation.

Figure 2:
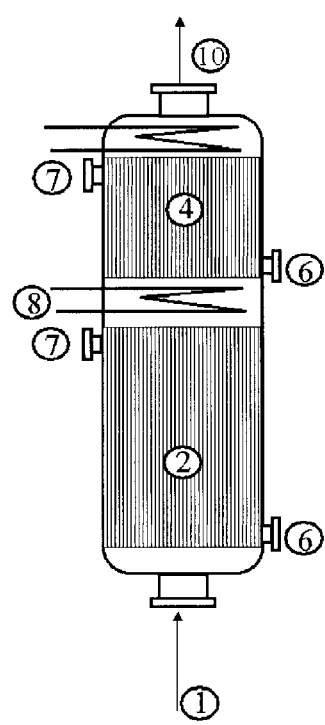

With reference to FIGS. 1 and 2, in a conventional process for the oxidation of propylene to acrylic acid in two stages in a single reactor, a gas mixture 1 comprising propylene, steam, nitrogen and molecular oxygen is passed into a multitubular reactor from the bottom upward over a catalyst 2 for the oxidation of propylene. The mixture resulting from this reaction, comprising unreacted gases, the acrolein produced and by-products, subsequently passes over a catalyst 4 for the oxidation of acrolein to give acrylic acid. A mixture 10 comprising the acrylic acid produced, residual acrolein, unreacted gases, water and by-products is obtained. Liquid coolants circulate in 6 and 7, so as to maintain a reaction temperature which can be between 300° C. and 380° C. for the reaction for the oxidation of propylene to give acrolein and a temperature which can be between 260° C. and 320° C. for the oxidation of acrolein to give acrylic acid. A heat exchanger 8 which makes it possible to cool the reaction gases is placed downstream of the two oxidation stages, as in FIG. 1; preferably, the heat exchanger 8 of FIG. 1 is downstream of the reactor and not in the reactor, which facilitates the charging and discharging of the reactor. A second heat exchanger 8 can be placed between the two catalytic beds, as represented in FIG. 2, making it possible to cool the intermediate gas mixture.

Figure 3:
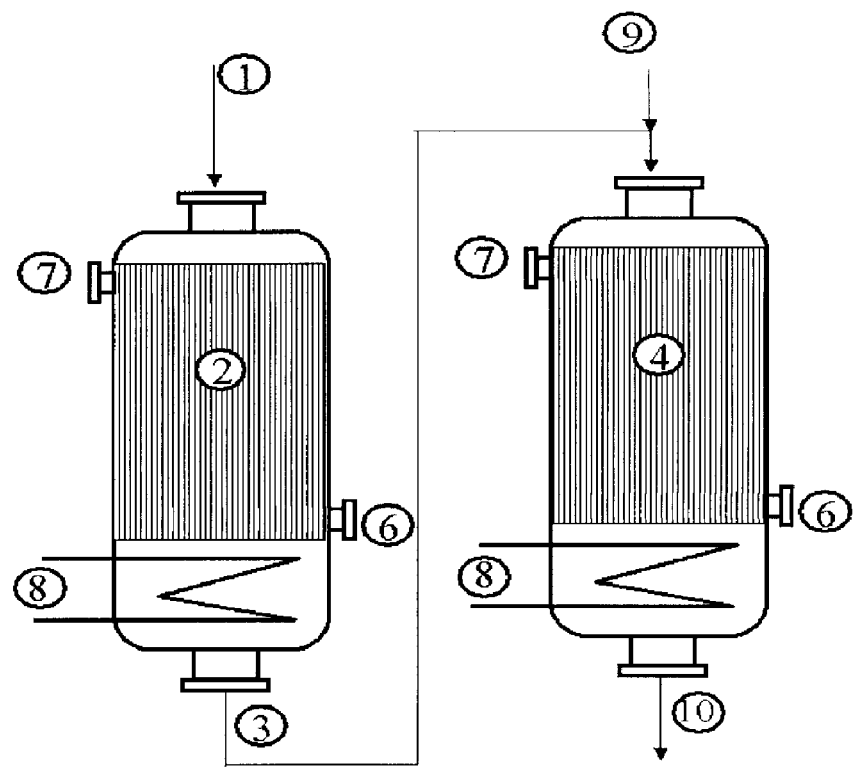

With reference to FIG. 3, in a conventional process for the oxidation of propylene to give acrylic acid in two stages in two consecutive reactors, a gas mixture 1 comprising propylene, steam, nitrogen and molecular oxygen is passed into a first multitubular reactor from the top downward over a catalyst 2 for the oxidation of propylene. The mixture 3 resulting from this reaction, comprising the unreacted gases, the acrolein produced and by-products, feeds a second reactor comprising a catalyst 4 for the oxidation of acrolein to give acrylic acid. The second reactor is optionally fed at 9 with oxygen or air. A mixture 10 comprising the acrylic acid produced, residual acrolein, the unreacted gases, water and by-products is obtained. Liquid coolants circulate in 6 and 7, so as to maintain a reaction temperature which can be between 300° C. and 380° C. for the reaction for the oxidation of propylene to give acrolein and a temperature of between 260° C. and 320° C. for the oxidation of acrolein to give acrylic acid. A heat exchanger 8 which makes it possible to cool the reaction gases resulting from the first stage is placed in the bottom of the first reactor. A second heat exchanger 8 is placed downstream of the two oxidation stages. The exchangers 8 can be outside the reactors.

Figure 4:
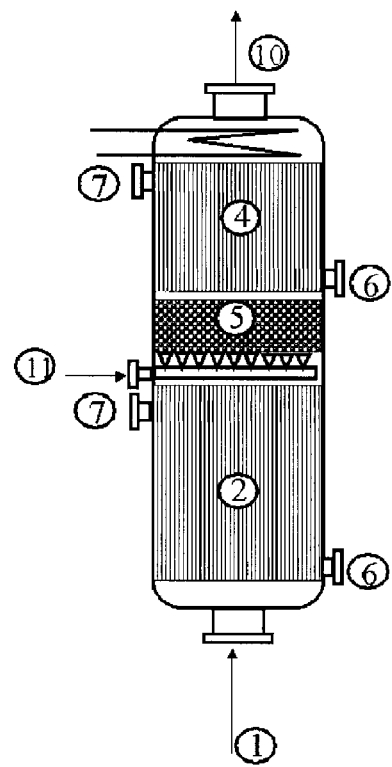
FIGS. 4 and 5 diagrammatically represent different configurations corresponding to embodiments of the process according to the invention.

In accordance with a first embodiment of the process according to the invention, illustrated diagrammatically in FIG. 4, the heat exchanger 8 in the conventional configuration of FIG. 2, which is placed between the two catalytic beds and which makes it possible to cool the gas mixture resulting from the reaction for the oxidation of propylene to give acrolein, is replaced with a stage of dehydration of glycerol. This stage consists in passing a mixture 11, composed of glycerol in the form of a vaporized aqueous solution and optionally of oxygen, at the same time as the gas mixture exiting from the oxidation region comprising the catalyst 2 for the oxidation of propylene to give acrolein, over a catalyst 5 for the dehydration of glycerol. A mixture of acrolein, resulting both from the reaction for the oxidation of propylene and from the reaction for the dehydration of glycerol, and also the by-products resulting from these two reactions, is obtained at the outlet of the region comprising the catalyst 5. This mixture subsequently passes over the catalyst 4, over which the acrolein is oxidized to give acrylic acid. A mixture 10 comprising the acrylic acid produced, residual acrolein, the unreacted gases, water and by-products is obtained.

Figure 5:
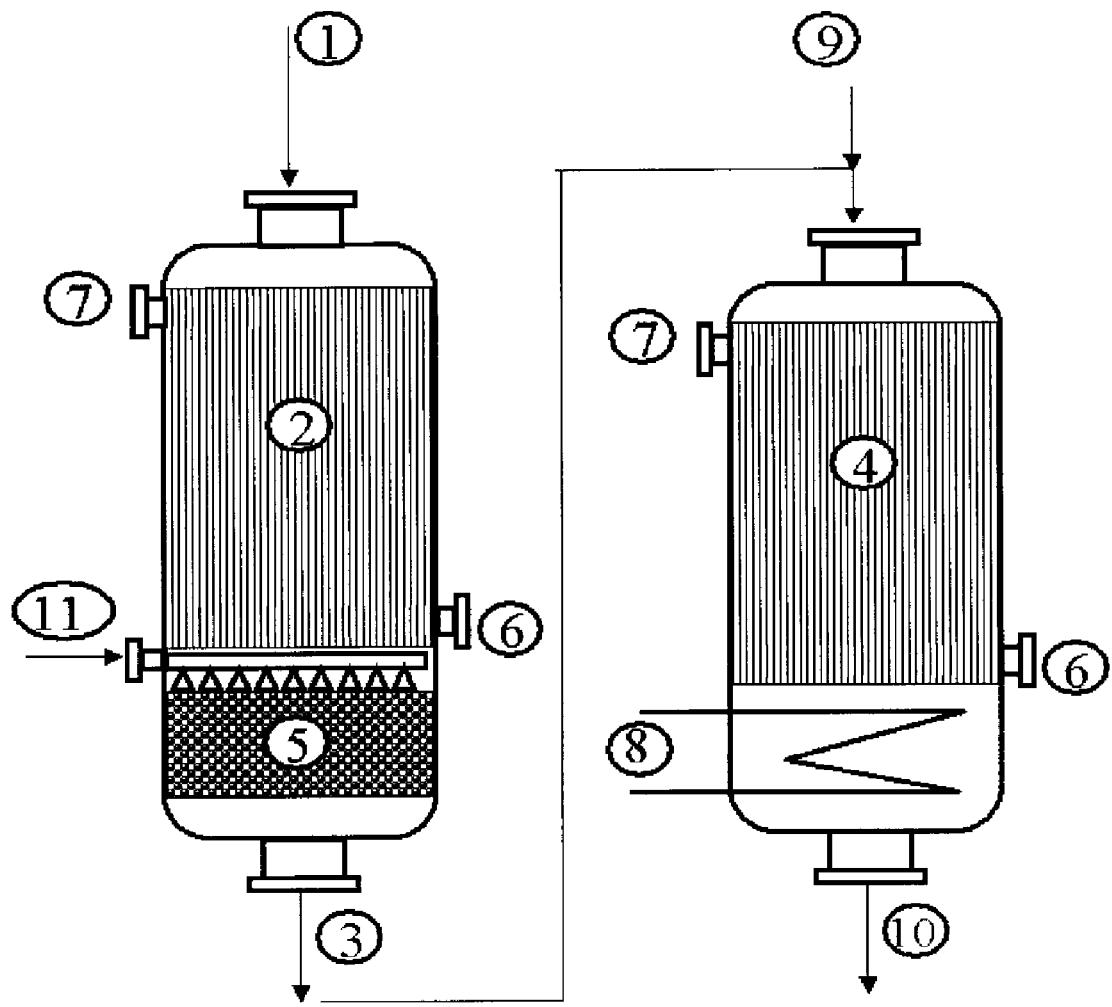

In accordance with a second embodiment of the process of the invention, illustrated diagrammatically in FIG. 5, the heat exchanger 8 placed downstream of the first reactor in a conventional process for the oxidation of propylene to give acrylic acid in two stages in two consecutive reactors, as represented in FIG. 3, is replaced with a stage of dehydration of glycerol. This stage consists in passing a mixture 11, composed of glycerol in the form of a vaporized aqueous solution and optionally of oxygen, at the same time as the gas mixture exiting from the oxidation region comprising the catalyst 2 for the oxidation of propylene to give acrolein, over a catalyst 5 for the dehydration of glycerol. A mixture 3 of acrolein, resulting both from the reaction for the oxidation of propylene and from the reaction for the dehydration of glycerol, and also the by-products resulting from these two reactions, is obtained at the outlet of the region comprising the catalyst 5. This mixture 3 feeds the second reactor comprising the catalyst 4 over which the acrolein is oxidized to give acrylic acid. A mixture 10 comprising the acrylic acid produced, residual acrolein, the unreacted gases, water and by-products is obtained.

According to the process of the invention, it is possible to obtain an increase in productive output of acrylic acid of the order of 50 to 200% in comparison with conventional processes.

It is possible to envisage employing another endothermic reaction than that of the dehydration of glycerol in order to efficiently recover the heat of reaction for the oxidation of propylene to give acrolein. In particular, the oxydehydration reaction of propane-1,3-diol or the dehydration of propan-1-ol or propan-2-ol are also advantageous from some angles, more particularly if the bed of dehydration catalyst is placed upstream of the reactor for the oxidation of propylene to give acrolein. This is because the dehydration of propane-1,3-diol can result in allyl alcohol which, in its turn, can be oxidized over the catalyst for the oxidation of propylene to give acrolein. Propan-1-ol or propan-2-ol can be dehydrated to give propylene and can subsequently be oxidized to give acrolein over the oxidation catalyst.

The following examples illustrate the present invention without, however, limiting the scope thereof.

In the examples, the products formed, acrolein and acrylic acid, are analyzed by chromatography on an EC-1000 capillary column fitted to an HP6980 chromatograph equipped with an FID detector. Quantitative analysis is carried out with an external standard.

Example 1

Use is made of a reactor configuration in which the glycerol is cofed with the gas mixture comprising the propylene from the top downward and which comprises three beds of catalyst. The Pyrex reactor is equipped with a sintered glass in order to retain the catalyst.

A weight of 5 g of catalyst for the oxidation of acrolein to give acrylic acid with the reference ACS4 (from Nippon Shokubai), reduced to a powder in a particle size of 100 to 160 microns and diluted with 5 ml of silicon carbide with a particle size of 0.125 mm, is first of all charged. Subsequently, 9 ml of silicon carbide with a particle size of 0.5 mm are charged. Subsequently, 6.498 g of catalyst for the oxidation of propylene to give acrolein with the reference ACF4 (from Nippon Shokubai), diluted with 7 ml of silicon carbide with a particle size of 0.125 mm, are charged. Subsequently, different beds of silicon carbide are charged, so as to separate the catalyst for the oxidation of propylene from the dehydration catalyst and to independently control their temperature: 2 ml with a particle size of 0.125 mm, then 7 ml with a particle size of 0.5 mm and again 2 ml with a particle size of 0.125 mm, and finally 1 ml with a particle size of 0.062 mm. Subsequently, 1.537 g of dehydration catalyst with the reference Z1044 (tungstated zirconia from DaIchi Kigenso KK), diluted with 4 ml of silicon carbide with a particle size of 0.062 mm, are charged. Finally, the reactor is made up to height with silicon carbide with a particle size of 0.125 mm (2 ml) and 0.5 mm, then 1.19 mm.

The reactor is subsequently connected to the test part. The temperatures of the three layers of catalyst are independently regulated at 305° C. for the two upper layers for the dehydration of glycerol and the oxidation of propylene and at 280° C. for the lower layer for the oxidation of acrolein to give acrylic acid.

The reactor is fed with a gas mixture of propylene/oxygen/helium-krypton/water-glycerol with hourly molar flow rates (expressed as micromoles per hour) of 30 089/55 584/288 393/water: 53 489—glycerol: 4509. The helium-krypton gas mixture comprises 4.92% of krypton, which acts as internal standard. The water-glycerol mixture comprises 30% by weight of glycerol. These conditions represent a total molar flow rate of $C_3$ compounds (propylene+glycerol) of 34 598 micromol/h.

The effluents are collected at the outlet of the reactor via a cold trap comprising ice and the acrolein and the acrylic acid produced are quantitatively determined by chromatographic analysis.

The effluents are accumulated in the trap for a time of 80 minutes. The noncondensable gases are analyzed throughout the duration of the assessment. The amount of acrolein produced is 503 micromol/h and the amount of acrylic acid is 26 103 micromol/h.

Example 2

Comparative

Example 1 is repeated but the aqueous glycerol solution is replaced with pure water. The molar flow rates of the reactants are then: propylene/oxygen/helium-krypton/water-glycerol: 30 089/55 584/288 393/water: 76 666—glycerol: 0 (micromol/h).

The effluents are accumulated in the trap for a time of 78 minutes. The noncondensable gases are analyzed throughout the duration of the assessment. The amount of acrolein produced is 457 micromol/h and the amount of acrylic acid is 23 257 micromol/h.

Example 3

Comparative

Example 2 is repeated but while replacing the dehydration catalyst with silicon carbide. The same feed conditions are used.

The effluents are accumulated in the trap for a time of 75 minutes. The noncondensable gases are analyzed throughout the duration of the assessment. The amount of acrolein produced is 521 micromol/h and the amount of acrylic acid is 23 363 micromol/h.

Example 4

Use is made of a reactor configuration comprising three beds of catalyst with a feed of the gas mixture comprising propylene from the top downward and an intermediate feed for the glycerol solution. The Pyrex reactor is equipped with a sintered glass for retaining the catalyst.

A weight of 5 g of catalyst for the oxidation of acrolein to give acrylic acid with the reference ACS4 (from Nippon Shokubai), reduced to a powder in a particle size of 100 to 160 microns and diluted with 5 ml of silicon carbide with a particle size of 0.125 mm, is first of all charged. Subsequently, 9 ml of silicon carbide with a particle size of 0.5 mm are charged. Subsequently, a weight of 1.578 g of catalyst for the dehydration of glycerol with the reference Z1044 (tungstated zirconia from DaIchi Kigenso KK), diluted with 4 ml of silicone carbide with a particle size of 0.062 mm, is charged.

Subsequently, different beds of silicon carbide are charged, so as to separate the dehydration catalyst from the catalyst for the oxidation of propylene and to independently control their temperature, and to make possible the injection of an aqueous solution of glycerol or of hydrated glycerol between the two beds of catalyst: 4 ml with a particle size of 0.125 mm, then 7 ml with a particle size of 0.5 mm and again 2 ml with a particle size of 0.125 mm. Subsequently, 6.578 g of catalyst for the oxidation of propylene to give acrolein with the reference ACF4 (from Nippon Shokubai), diluted with 7 ml of silicon carbide with a particle size of 0.125 mm, are charged. Finally, the reactor is made up to height with silicon carbide with a particle size of 0.125 mm (2 ml) and 0.5 mm, then 1.19 mm.

The reactor is subsequently connected to the test plant. The temperatures of the layers of catalyst are independently regulated at 260° C. for the lower layers for the dehydration of glycerol and for the oxidation of acrolein to give acrylic acid and at 305° C. for the upper layer for the oxidation of propylene to give acrolein.

The reactor is fed with a gas mixture of propylene/oxygen/helium-krypton/water at its top part with hourly molar flow rates (expressed in micromoles per hour) of 30 089/55 584/288 393/76 666. The helium-krypton gas mixture comprises 4.92% of krypton, which acts as internal standard. A water-glycerol mixture comprising 80% by weight of glycerol is fed between the layer of catalyst for the oxidation of propylene and the dehydration catalyst, with a glycerol/water flow rate of 4530/5794 (micromol/h). These conditions represent a total molar flow rate of $C_3$ compounds (propylene+glycerol) of 34 619 micromol/h.

The effluents are collected at the outlet of the reactor via a cold trap comprising ice and the acrolein and acrylic acid produced are quantitatively determined by chromatographic analysis.

The effluents are accumulated in the trap for a time of 84 minutes. The noncondensable gases are analyzed throughout the duration of the assessment. The amount of acrolein produced is 389 micromol/h and the amount of acrylic acid is 26 360 micromol/h. The residual propylene is 2613 micromol/h.

Example 5

Example 4 is repeated but using a 95% by weight glycerol solution (hydrated glycerol).

The hourly molar flow rates (in micromoles per hour) of the constituents of the mixture are as follows: propylene/oxygen/helium-krypton/water 30 089/55 584/288 393/76 666 for the top feed and glycerol/water 8220/2205 for the intermediate feed. These conditions represent a total molar flow rate of $C_3$ compounds (propylene+glycerol) of 38 309 micromol/h.

The effluents are accumulated in the trap for a time of 81 minutes. The noncondensable gases are analyzed throughout the duration of the assessment. The amount of acrolein produced is 633 micromol/h and the amount of acrylic acid is 29 898 micromol/h. The residual propylene is 2803 micromol/h.

Example 6

Example 4 is repeated but using a 70% by weight glycerol solution.

The hourly molar flow rates (in micromoles per hour) of the constituents of the mixture are as follows: propylene/oxygen/helium-krypton/water 30 089/55 584/288 393/76 666 for the top feed and glycerol/water 6350/13 923. These conditions represent a total molar flow rate of $C_3$ compounds (propylene+glycerol) of 36 439 micromol/h.

The effluents are accumulated in the trap for a time of 78 minutes. The noncondensable gases are analyzed throughout the duration of the assessment. The amount of acrolein produced is 612 micromol/h and the amount of acrylic acid is 28 212 micromol/h. The residual propylene is 2702 micromol/h.

What is claimed is:

1. A process for the preparation of acrylic acid from propylene comprising a first stage of oxidation of propylene to give acrolein and a second stage of oxidation of the acrolein to give acrylic acid, further comprising a stage of dehydration of glycerol in the presence of said propylene to give acrolein.

2. The process as claimed in claim 1, characterized in that the dehydration of glycerol is carried out in the gas phase in the presence of a catalyst selected from the group consisting of sulfated zirconias, phosphated zirconias, tungstated zirconias, silica zirconias, sulfated titanium, tin oxides, phosphated aluminas and phosphated silicas.

3. The process as claimed in claim 1, characterized in that molecular oxygen is added for the stage of dehydration of the glycerol.

4. The process as claimed in claim 1, characterized in that the glycerol is injected in the liquid form or in the gas form.

5. The process as claimed in claim 1, characterized in that use is made of pure glycerol or glycerol in the form of a concentrated or dilute aqueous solution.

6. The process as claimed in claim 1, characterized in that the oxidation of the propylene is carried out in the presence of a thermal ballast.

\* \* \* \* \*